United States Patent [19]

Mather et al.

[11] 3,998,255
[45] Dec. 21, 1976

[54] BREATHER ASSEMBLY FOR A SEALED CONTAINER

[75] Inventors: Byron L. Mather, Milwaukee; Raymond H. Johnston, Greenfield, both of Wis.

[73] Assignee: Plastronics, Inc., Milwaukee, Wis.

[22] Filed: Sept. 17, 1975

[21] Appl. No.: 614,135

[52] U.S. Cl. .................................. 150/1; 55/310; 55/524; 128/275
[51] Int. Cl.[2] ...................................... B65D 33/00
[58] Field of Search ............... 150/1; 128/275, 283, 128/295; 55/310, 514, 524, 528

[56] References Cited

UNITED STATES PATENTS

| | | | |
|---|---|---|---|
| 3,575,170 | 4/1971 | Clark | 128/275 |
| 3,803,810 | 4/1974 | Rosenberg | 55/528 UX |

Primary Examiner—Donald F. Norton
Attorney, Agent, or Firm—Michael, Best & Friedrich

[57] ABSTRACT

A breather assembly for a sealed container such as a bedside drainage bag, such bag being made of sheets of polyvinyl chloride plastic which material has the characteristics of receiving an electronic weld. A breather element is positioned between one face of the container wall and a retaining ring. The wall and ring have openings therein positioned in alignment with each other. The breather element retaining ring is comprised of a non-porous flexible material such as polyvinyl chloride having the characteristics of receiving an electronic weld. The breather element is made from a material comprised of a woven nylon substrate with a coating of a copolymer of polyvinyl chloride and acrylonitrile which material is effective to allow free passage of air therethrough while at the same time effectively resisting the flow of liquid therethrough. Such material also has the characteristics of receiving an electronic weld. The parts are sealed to each other by the application of an electronic weld applied to the peripheral portions of the ring and filter element. Such weld will fuse the retaining ring to the wall of the container and to the breather element to thereby seal the parts together and prevent any tendency of liquid in the container to flow around the edge of the breather element.

6 Claims, 3 Drawing Figures

U.S. Patent  Dec. 21, 1976  3,998,255
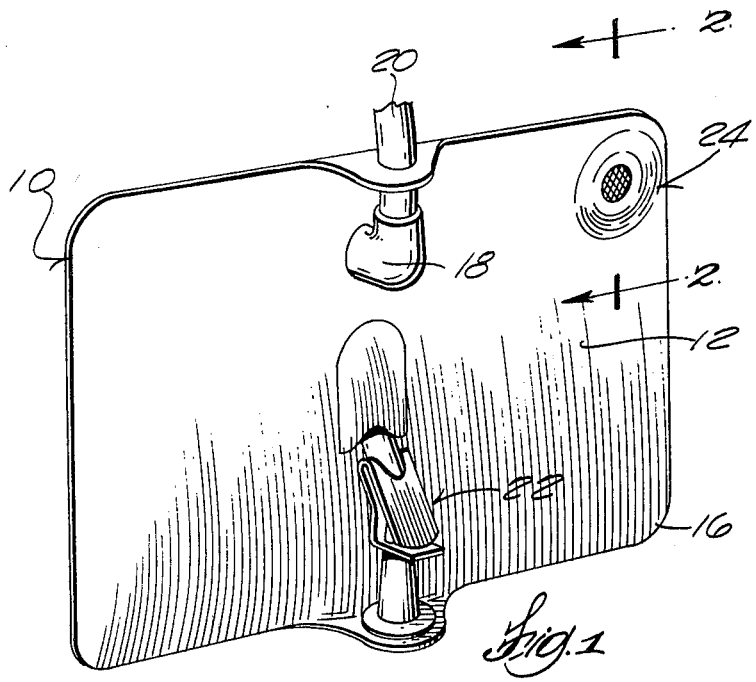
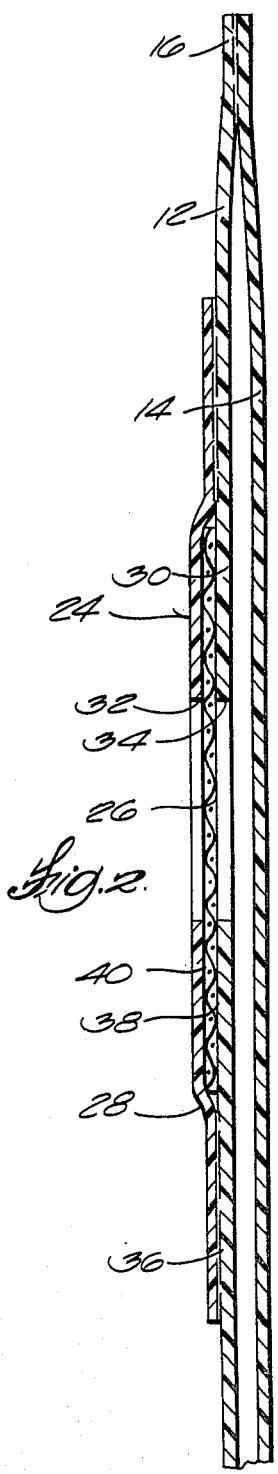
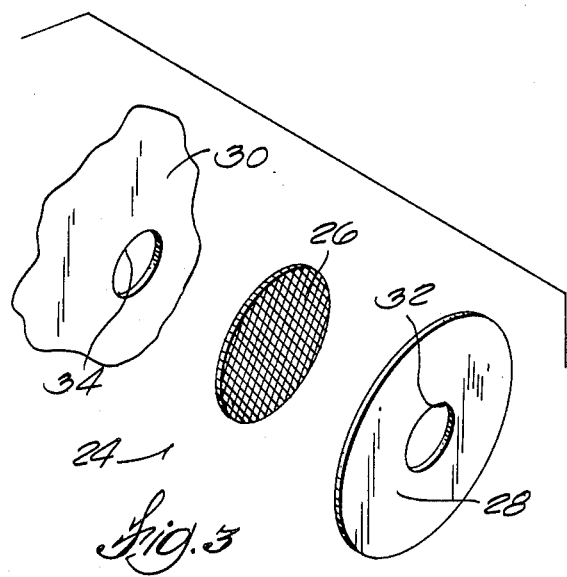

BREATHER ASSEMBLY FOR A SEALED CONTAINER

BACKGROUND OF THE INVENTION

1. Field of the Invention

This invention relates to a breather assembly for a closed container and more particularly to a simplified breather assembly for use on a bedside drainage bag of the type used in a closed catheter system.

2. Description of the Prior Art

The most pertinent prior art known to applicant is that shown in U.S. Pat. No. 3,575,170. The assembly of this invention provides a greatly simplified arrangement comprised of a smaller number of parts which can be assembled with a single electronic weld step as compared to that shown in such patent.

SUMMARY OF THE INVENTION

A breather assembly for a sealed container having a breather opening therein. The container is made of a non-porous plastic material having the characteristics of receiving an electronic weld. A breather element is provided which is made from a material adapted to allow free passage of gas therethrough and to resist passage of liquid therethrough, such breather element having the characteristics of receiving an electronic weld. A breather element retaining ring is also provided which ring has an opening in the central portion thereof and is made from a non-porous plastic material having the characteristics of receiving an electronic weld. The retaining ring is mounted on the wall of the container with the opening therein in substantial alignment with the breather opening in the container. The breather element is mounted between the ring and the wall of the container with the ring overlying the breather element and with the ring fused by electronic welding to the wall of the container and to the breather element to thereby seal the parts together and prevent any tendency of liquid in the container to flow around the edge of the breather element.

DESCRIPTION OF THE DRAWINGS

FIG. 1 is a perspective view of a bedside drainage bag incorporating the present invention;

FIG. 2 is an enlarged fragmentary sectional view of the breather assembly of this invention taken along line 2—2 of FIG. 1; and FIG. 3 is an exploded view showing the various components of the breather assembly.

DESCRIPTION OF THE PREFERRED EMBODIMENT

Referring to the drawings in detail, FIG. 1 shows a bedside drainage bag 10 designed for use in a closed catheter system. Bedside drainage bag 10 is preferably made from two sheets of polyvinyl chloride plastic 12, 14 which are sealed to each other around the peripheral edges thereof as at 16, preferably by an electronic welding procedure to provide a sealed container. The drainage bag is provided with an inlet fitting 18 having a tube 20 connected thereto for conducting the flow of fluid into the bag. Fitting 18 and tube 20 are also preferably made from polyvinyl chloride material. Attached to tube 20 is a so-called "retention" type catheter (not shown) of any suitable design. The bag 10 is also provided with a drainage assembly 22 designed for periodically draining the bag of its contents. The drainage assembly 22 does not form a part of this invention, and, therefore, a detailed description of such assembly will not be made herein.

A catheter attached to tube 18 is adapted to be passed through the urethra into the bladder of a patient and when so positioned forms an essentially closed or air tight system with respect to the drainage bag 10. Plastic drainage bags of the type shown herein when put into use are generally in a flat conditon with the walls 12 and 14 thereof in close contact with each other. Thus, when the bag is put into use, there is generally little or no air in the bag at the beginning of the drainage operation.

It will be appreciated, therefore, that as drainage of fluid through tube 18 into the bag occurs, the flexible walls of the bag will be bulged outwardly, thereby increasing the volume of "air" space inside the bag. This expansion of the bag in a closed system will tend to create a vacuum within the system which condition may be very detrimental to the user due to the possibility of resultant serious injury to the bladder. It is essential, therefore, that some means be provided to prevent such a "vacuum" condition from occurring.

Such a means is provided by a specially designed breather assembly 24 mounted in the upper portion of the bag as shown in FIG. 1. As will be explained hereinafter, breather assembly 24 functions to allow free passage of air in and out of bag 10 while at the same time prevents flow of liquid therethrough under normal circumstances. The breather assembly also functions to filter out bacteria from the air flowing into the bag to prevent such bacteria from reaching the patient's bladder.

As shown in FIGS. 2 and 3, the breather assembly 24 is comprised of three components, namely, a breather element 26, a breather element retaining ring 28 and a portion 30 of the face of wall 12 of the bag 10.

Retainer 28 and wall portion 30 are provided with openings 32 and 34 respectively of substantially equal diameter.

In the preferred embodiment breather element 26 is made from a material comprised of a woven substrate of synthetic material such as nylon with a coating of a copolymer such as polyvinyl chloride. In the commercial embodiment of this invention the coating applied to the woven substrate contains some acrylonitrile in addition to the polyvinyl chloride. Such material provides a microporous hydrophobic structure which is effective to allow free passage of air therethrough while at the same time effectively resisting the flow of liquid therethrough. Also of significance is the fact that the preferred material of the filter as specified above has the characteristic of receiving an electronic weld. More specifically such material has a high dielectric loss wherein a molecular disturbance is created by the high-frequency energy causing the molecules in the material to vibrate against each other at a rate sufficient to create frictional melting at the interfaces.

Breather element retaining ring 28 and wall 12 of bag 10 including portion 30 thereof are comprised of a non-porous flexible material such as polyvinyl chloride having the characteristics of receiving an electronic weld.

The breather assembly 24 is assembled and mounted on the drainage bag 10 as best shown in FIG. 2. The breather element 26 is positioned between face 30 of the bag and retaining ring 28 with openings 32 and 34 of the ring and bag, respectively, in alignment with each other. The parts are sealed to each other by the application of an electronic weld applied to the peripheral portions of both ring 28 and filter element 26. Such electronic weld will cause the outer peripheral portion of ring 28 to be sealed to the portion 30 of the bag as indicated by reference numeral 36. The weld will also cause the inner peripheral portion of ring 28 and surface 30 of the bag to be sealed to both sides of the outer peripheral portion of element 26 as indicated by reference numerals 38 and 40. Such electronic welding procedure producing the seals as described above will serve to securely seal the filter element 26 in the overall assembly to thus prevent any tendency of liquid to flow around the edge of the breather element in the completed assembly. It will be appreciated that instead of mounting the breather assembly on the outside face of wall 12 of the drainage bag as shown in the drawings it could just as well be mounted on the inside face of wall 12.

The breather assembly 24 thus assembled in the bag 10 functions to permit the free passage of air from the atmosphere into the inside of the bag as the bag expands due to flow of fluid therein through tube 20 from the patient. Thus any tendency of a vacuum to be created in the closed system will be alleviated. Also, as indicated above, breather assembly 24 functions to filter out bacteria in the air flowing into the bag. It is also noted that any tendency of the fluid inside the bag to flow out through the breather assembly 24 will be prevented. This could be a problem when handling the filled bag for drainage thereof or for any other reason.

The above described assembly provides a simple and effective breather assembly arrangement which is comprised of a minimum number of parts and which can be assembled with a single electronic weld step.

We claim:

1. A breather assembly for a sealed container having a breather opening therein and said container being made of non-porous plastic material having the characteristics of receiving an electronic weld:

a breather element adapted to permit free passage of gas therethrough and to resist passage of liquid therethrough, said breather element comprising a woven substrate of synthetic material with a coating of plastic material, said plastic material having the characteristics of receiving an electronic weld;

a breather element retaining ring having an opening in the central portion thereof, said retaining ring being made from a non-porous plastic material having the characteristics of receiving an electronic weld; and said retaining ring mounted on the wall of the container with the opening therein in substantial alignment with the breather opening in the wall of the container, said breather element mounted between said ring and said wall with the retaining ring overlying said breather element, said retaining ring being fused by electronic welding to said wall and said element to thereby seal the parts together and prevent any tendency of liquid in the container to flow around the edge of the breather element.

2. A breather assembly according to claim 1 in which said container and said breather element retainer ring are made of polyvinyl chloride material and said plastic coating on said woven substrate of synthetic material is a copolymer material.

3. A breather assembly according to claim 2 in which said synthetic material is nylon and said copolymer material is polyvinyl chloride.

4. A breather assembly according to claim 3 in which said polyvinyl chloride coating includes some acrylonitrile.

5. A breather assembly according to claim 1 in which the outer peripheral portion of said breather element is fused to the wall of the container.

6. A breather assembly according to claim 1 in which the openings in said container wall and retaining ring are circular and in which said breather element retaining ring and breather element are circular.

* * * * *